(12) United States Patent
Oh

(10) Patent No.: US 8,086,473 B2
(45) Date of Patent: Dec. 27, 2011

(54) METHOD AND SYSTEM FOR MANAGING OPERATIONS AND PROCESSES IN HEALTHCARE DELIVERY IN A HOSPITAL

(76) Inventor: Hilario L. Oh, Oakland Township, MI (US)

( * ) Notice: Subject to any disclaimer, the term of this patent is extended or adjusted under 35 U.S.C. 154(b) by 469 days.

(21) Appl. No.: 12/408,091

(22) Filed: Mar. 20, 2009

(65) Prior Publication Data

US 2010/0241452 A1    Sep. 23, 2010

(51) Int. Cl.
    *G06Q 50/00*    (2006.01)
(52) U.S. Cl. .......................................... 705/3; 705/7.26
(58) Field of Classification Search .................. 705/2–3, 705/7.11–42
    See application file for complete search history.

(56) References Cited

U.S. PATENT DOCUMENTS

| | | | |
|---|---|---|---|
| 7,904,192 B2* | 3/2011 | Chua et al. .................... 700/100 |
| 2004/0019501 A1* | 1/2004 | White et al. ....................... 705/2 |
| 2004/0249676 A1* | 12/2004 | Marshall et al. .................... 705/2 |
| 2007/0153803 A1 | 7/2007 | Lakshmanaurthy et al. |
| 2009/0112677 A1* | 4/2009 | Rhett ................................ 705/8 |
| 2009/0119126 A1* | 5/2009 | Johnson et al. ................... 705/2 |

OTHER PUBLICATIONS

Borghetti, A., et al., "A Two-Stage Scheduler of Distributed Energy Resources" (Jul. 2007), pp. 2168-2173.
Kolb, Erik M.W., et al., Effect of Coupling Between Emergency Department and Inpatient Unit on the Overcrowding in Emergency Department (2007), pp. 1586-1593.
Hochbaum, Dorit S., "The Scheduling Problem" (1999), Website: http//riot.ieor.berkeley.edu/riot/applications/scheduling/index.html, accessed Mar. 17, 2009.
Peck, Jordan, et al., A Discrete Event Simulation Approach to Optimizing Design and Use of Fast Track in an Emergency Department (IEEE Winter 2007 Conference).
Peck, Jordan, et al., "Improving Emergency Department Patient Flow Through Optimal Fast Track Usage" (2008), Abstract.
Peck, Jordan, et al., "Securing the Safety Net: Applying Manufacturing Systems Methods Towards Understanding and Redesigning a Hospital Emergency Department" (Jun. 2008), Abstract.

* cited by examiner

*Primary Examiner* — Gerald J. O'Connor
*Assistant Examiner* — Mark Holcomb
(74) *Attorney, Agent, or Firm* — Harness, Dickey & Pierce, P.L.C.

(57) ABSTRACT

A method and system for managing healthcare delivery is presented. The method includes receiving data related to patients and the patients' scheduled procedures. Based on the data, a queue is generated for screening the patients. The patients are screened in accordance with the screening queue. Once screened, data related to tracking the patients is obtained. The tracking data is used to generate a tracking queue. The patients are tracked in relation to the tracking queue.

24 Claims, 12 Drawing Sheets

2/19/09        SURGERY SCHEDULE                    2/23/2009  H02   7:30    oprr070  rec4
        Patient: XXXXXXXX
               OPR Preference Card Detail Maintenance                      OPRR301
                    CPD INSTRUMENTS                                          FMT06

DOC NO:  XXXXXXXXXXXX        CASE CART NO:     CHARGE CODE:  3502142
PROC NO: 66266    DESCRIPTION: LAPAROSCOPIC ASSISTED VAGINAL HYSTERECTO
                               MY  (745AM/WATCH USE RM 10 ONLY)

QTY  AREA  ITEM #     CPD INSTRUMENTS
 1    CC   75460      GYN VAG PLASTY SET
 1    CC   75227      G  S  GYN LAPAROSCOPIC
 1    CC   75231      G  S  GYN SCOPE RIGID  0 DEG  10MM
 1    CC   75270      GYN DC SET
 1    CC   99899      POWER  STRYKER  CAMERA  HEAD   W  COUPLER1
 1    CC   75753      G  S  GYN SCOPERIGID  0 DEG5X29CM
 1    CC   75992      G  S  STRYKER  SUCTIONIRRIGATION   SET
 1    CC   96191      TRAY MAYO  12 X 19 X

Figure 8

METHOD AND SYSTEM FOR MANAGING OPERATIONS AND PROCESSES IN HEALTHCARE DELIVERY IN A HOSPITAL

FIELD

The present disclosure relates to a computer implemented system and method for managing operations and processes in healthcare delivery in a hospital.

BACKGROUND

This section provides background information related to the present disclosure which is not necessarily prior art.

Healthcare delivery in today's hospitals is a complex task. A major source of complexity derives from the interdependency and interaction between multiple operations or units in the hospital, e.g. inpatient units, emergency departments (EDs), operating rooms (ORs), central sterilization department (CSD) and intensive care units (ICUs). For example, inefficient boarding in an inpatient unit that results in crowding in the ED is a manifestation of interdependency among operations in a hospital. Boarding is the term used to describe scheduling a patient for a procedure or otherwise entering the patient into the system of a particular unit. Another related source of complexity derives from the interdependency and interaction between various processes and resources required to complete a task within a single operation or unit. For example, in an OR, providing a greater degree of accessibility to surgeons or patients at the expense of utilization or productivity is an example of an interaction among processes or resources within an operation. Thus, it should be apparent that because interaction and interdependence couple the operations and processes in healthcare delivery, there is a need to manage healthcare delivery as a system.

In managing a healthcare delivery system, one must consider the functional requirements of the operations that comprise the system and the design parameters that render the functional requirements mutually exclusive and free from interactions and interdependencies. As interactions and interdependencies of functional requirements are reduced, if not eliminated, the system becomes less complex. A functional requirement may be thought of as a desired objective, while a design parameter may be thought of as how to achieve a functional requirement. In defining a set of functional requirements for a healthcare system, one should ensure to craft a list of functional requirements that is exhaustive and non-frivolous. Defining functional requirements will ensure that the operations are effective and defining design parameters will ensure that operations are efficient.

In the healthcare industry there are many functional requirements. The most common functional requirements in operations and their corresponding metrics are:

1) raise throughput—the number of jobs completed per unit time, the goal is to maximize this metric;
2) reduce length of stay—the length of time a patient stays in the system, the goal is to minimize this metric;
3) efficient use of resources—the level of capacity utilization, the goal is to maximize this metric;
4) reduce wait time—the length of time between the arrival of a job and the commencement of processing the job, the goal is to minimize this metric;
5) deliver service on time—the difference between the time a job is due and the actual time the job is finished, the goal is to minimize this metric; and
6) deliver service reliably—the consistency in delivering a job on time, the goal is to maximize this metric.

The design parameters for the functional requirements described above may include the following process variables:

1) processing time—the length of time to process a job;
2) due date—the date by which a task must be completed;
3) capacity—the amount of resources available, e.g. the amount of available beds in a unit;
4) slack time—time until due date minus processing time; and
5) completion time—the time when a job is actually finished.

As can be seen from the above definitions, two or more functional requirements may depend on the same process variables. For example, both throughput and length of stay are dependent on the processing time of a patient, that is—the amount of time it takes to diagnose and treat a patient. It logically follows that the two functional requirements cannot be independently satisfied by the same process variable. Thus, the two functional requirements, length of stay and throughput are coupled because they involve the same process variable. Similarly, deliver service on time and deliver service reliability are coupled, as the two functional requirements are dependent on the due date variable.

While tools and techniques to optimize functional requirements have been developed, these solutions do not take coupling into account. Instead, they address a specific functional requirement at the expense of other functional requirements. These trade-off schemes, which seek to mitigate the ill effect of the non-optimized functional requirement, result in sub-optimal coupled systems. Thus, there is a strong need for a system or tool to optimize coupled systems in the healthcare delivery industry.

SUMMARY

This section provides a general summary of the disclosure, and is not a comprehensive disclosure of its full scope or all of its features.

In one sense, a method for managing healthcare delivery is provided. The method comprises receiving patient data for two or more patients scheduled for a medical procedure, where a timeline for the medical procedure is in part derived from the patient data. The method further comprises determining a queue position in a screening queue for each patient using a first design parameter associated with the timeline for the medical procedure, where the screening queue indicates the order in which a screening process is administered to each patient. The method also includes screening the patients in accordance with the screening queue. The method further comprises determining for patients having completed the screening process medical testing required for the medical procedure based on information obtained during the screening process. The method also includes determining a queue position in a tracking queue for patients having completed the screening process using a second design parameter that is negatively correlated to the first design parameter and associated with the timeline for the medical procedure, where the tracking queue indicates the order in which patients are contacted to determine status of medical testing required for the medical procedure. The method finally includes tracking the medical testing required for each patient having completed the screening process in accordance with the tracking queue.

In a second sense, a computer implemented system for managing healthcare delivery is presented. The system comprises a data store storing patient data and patient tracking data. The system further comprising a first calculation module calculating a first priority value based on the patient data.

The system includes a second calculation module calculating a second priority value based on the patient data and patient tracking data.

Another area of applicability is in the central sterilization processing of surgical instruments Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 8 is an exemplary surgery schedule showing a procedure type and a instrument sets required for the procedure;

Corresponding reference numerals indicate corresponding parts throughout the several views of the drawings.

DETAILED DESCRIPTION

Example embodiments will now be described more fully with reference to the accompanying drawings.

An exemplary system for managing healthcare operations is presented. The healthcare management system is a computer implemented system that is configured to take into account functional requirements when scheduling patients. The system is comprised of a data store that stores patient data and at least one calculation module that determines a priority value for a given patient or job.

Figure 1:
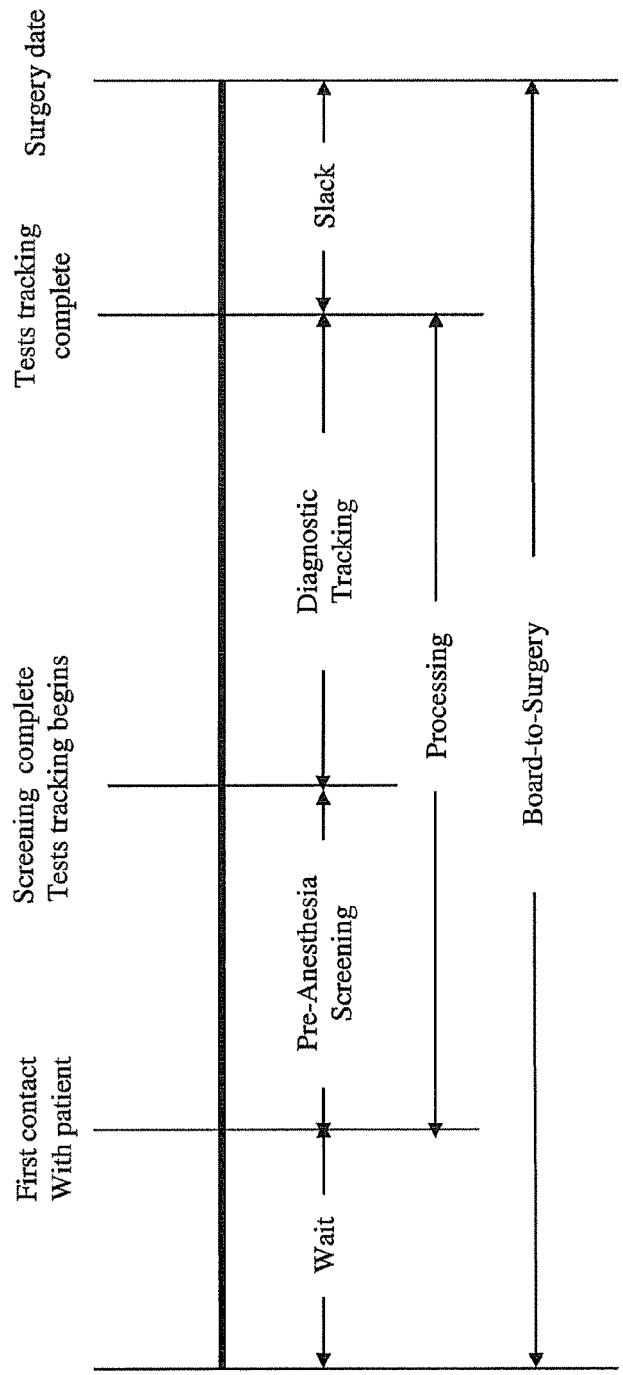
FIG. 1 is a diagram depicting a timeline of a pre-admissions testing job.

For exemplary purposes, the system is described with respect to a pre-admission testing (PAT) process for surgical patients. The PAT process is a critical step in the healthcare delivery industry, as the goal is to uncover a patient's preoperative conditions that may affect the scheduled surgical or medical procedure. Referring now to FIG. 1, a timeline 10 depicts the events that must be completed during the PAT process. The PAT process begins when a patient is boarded on the board date and ends when the patient is transferred to the operating room for the procedure on the surgery time. The boarding date may be the date a patient is actually scheduled for a surgery or medical procedure. The interceding time period is referred to as "board-to-surgery" time.

Once a patient is boarded, the patient must be screened by nurse or some other medical personnel. The time period between the board date and the first contact with the patient is referred to as wait time. During screening, a PAT nurse will ask the patient questions concerning her medical history and diagnosed conditions. For example, the PAT nurse may determine that the patient suffers from heart disease and thus, may need an EKG performed before the surgery may be performed. The screening portion is complete once the PAT nurse has learned of the patient's medical history and determined the patient's pre-procedure tests requirement; i.e., tracking requirements.

The tracking period begins once the medical staff develops the criteria for pre-procedure testing, based on the patient's preoperative condition and the planned surgical procedure. Once the tracking period is complete, the patient may be cleared for the planned surgical procedure. The tracking period may include a nurse contacting a patient to determine what pre-procedure medical tests have already been performed and, if so, where to collect the results of those tests. Furthermore, the nurse may determine what tests need to be completed as well as when and where those tests will be performed (e.g. the hospital, a specialist's office, or at the primary physician's office). The tracking period may also include scheduling a patient to come into the hospital for a test or actually obtaining the test results from a third party. Tracking requirements may be dependent on hospital policy or known medical procedure. For example, a hospital policy may be that any patient age 75 or older must have a complete blood analysis and an EKG performed prior to the scheduled procedure. Thus, after screening a patient and learning that the patient is older than 74, the PAT nurse must ensure that the required blood analysis and EKG are performed before the date of the surgery (typically all tests must be received at least two days before the surgery). The PAT nurse must, as part of the tracking process, contact the patient to determine which tests have been performed and which tests need to be scheduled. Upon learning that the patient has already had tests performed, the PAT nurse must contact the test provider and obtain the test results. The PAT nurse may also schedule the patient to come to the hospital for testing.

If the tracking process is not complete by the date of the procedure, the procedure must be rescheduled. Rescheduling a procedure wastes a tremendous amount of resources. Typically, the surgeons and doctors that were to perform the procedures do not have enough notice to fill the time slot of the surgery of the patient, thereby resulting in a loss of revenue for that time slot. Moreover, many of the tests will have to be repeated, as test results are normally only valid for 30 days or less. Additionally, the PAT nurse will have to re-track the patient. Thus, it is imperative that the tracking period be complete before the procedure or surgery date, also referred to as the due date.

The period between the end of the tracking period and the due date is referred to as slack time. The period ranging from the beginning of the screening process to the end of the tracking process is the processing time.

There are a number of design parameters, i.e. job ordering and sequencing policies, for scheduling a process, or job, at a healthcare facility such as a hospital. Given a stream of jobs, one must determine what the functional requirements are and what the design parameters are for processing the jobs. Hospitals typically employ an earliest-due-date (EDD) first policy as the design parameter for pre-admission testing. An earliest-due-date first policy can best be described as processing the job with the least time remaining until the scheduled procedure first. Hospitals choose this policy because the time available until the due date is generally viewed by healthcare providers as the best measure of urgency. In fact, it is an incomplete measure of urgency as explained below.

Figure 2:
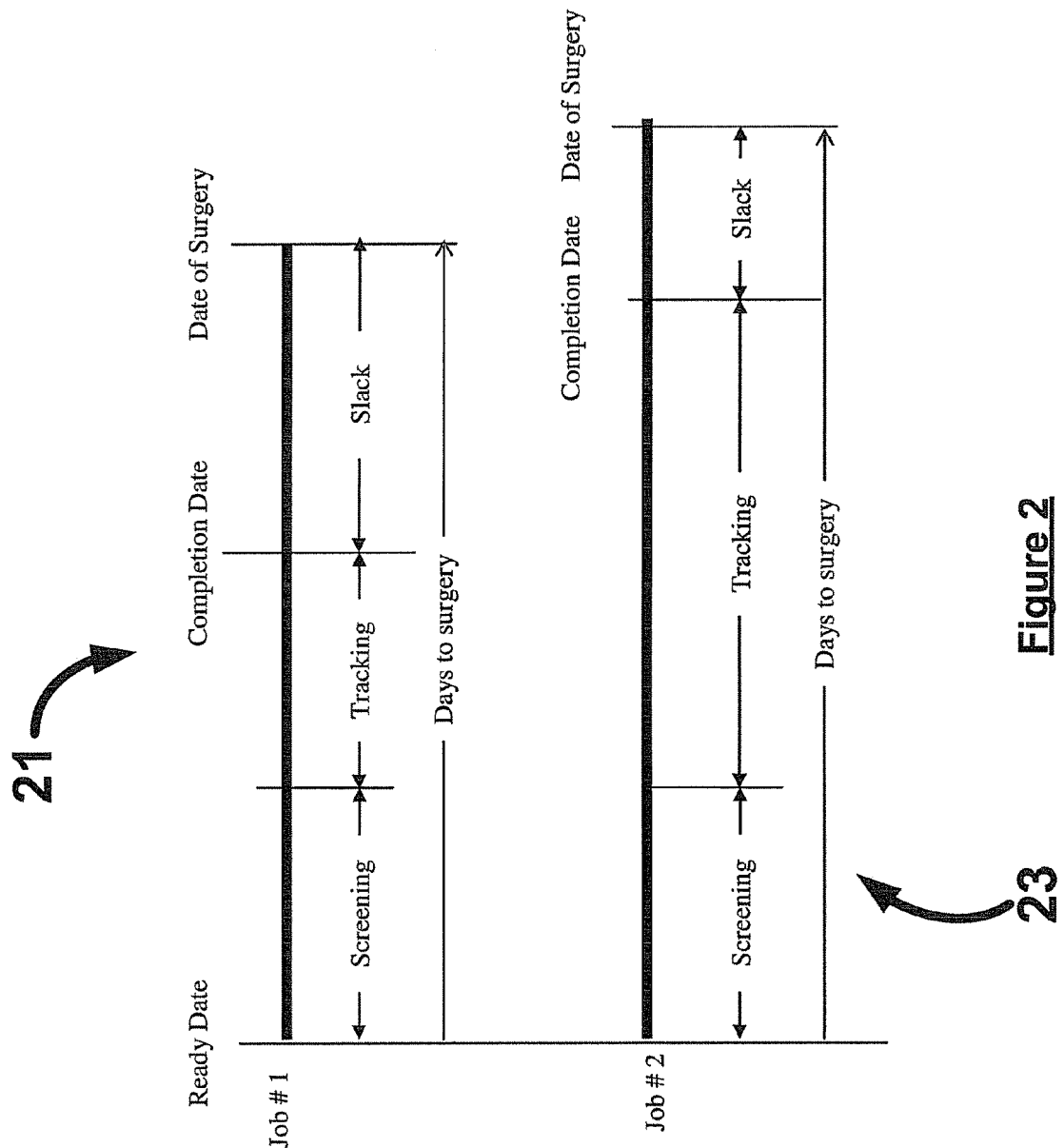
FIG. 2 is a diagram comparing the timelines of two pre-admissions testing jobs.

Referring to FIG. 2, two timelines 21 and 23 for two different jobs are shown from the commencement of the screening period to the due date. As can be seen, Job 1, shown in timeline 21, has an earlier due date than that of Job 2, shown in timeline 23. According to the earliest-due-date first policy, Job 1 is perceived as more urgent and will be processed first. Job 2, however, has a much longer tracking period. Thus, the likelihood of the tracking process not being complete in time for the surgery is greater for Job 2 then Job 1. Job 2 therefore is the more urgent and should be processed first. In other words, the relevant measure of urgency is Slack Time, measured by (Time to Due Date−Processing Time), as it takes both due date and processing time into account. If the desire is to schedule for urgency, then the least-slack-time (LST) first policy should be implemented.

Figure 3:
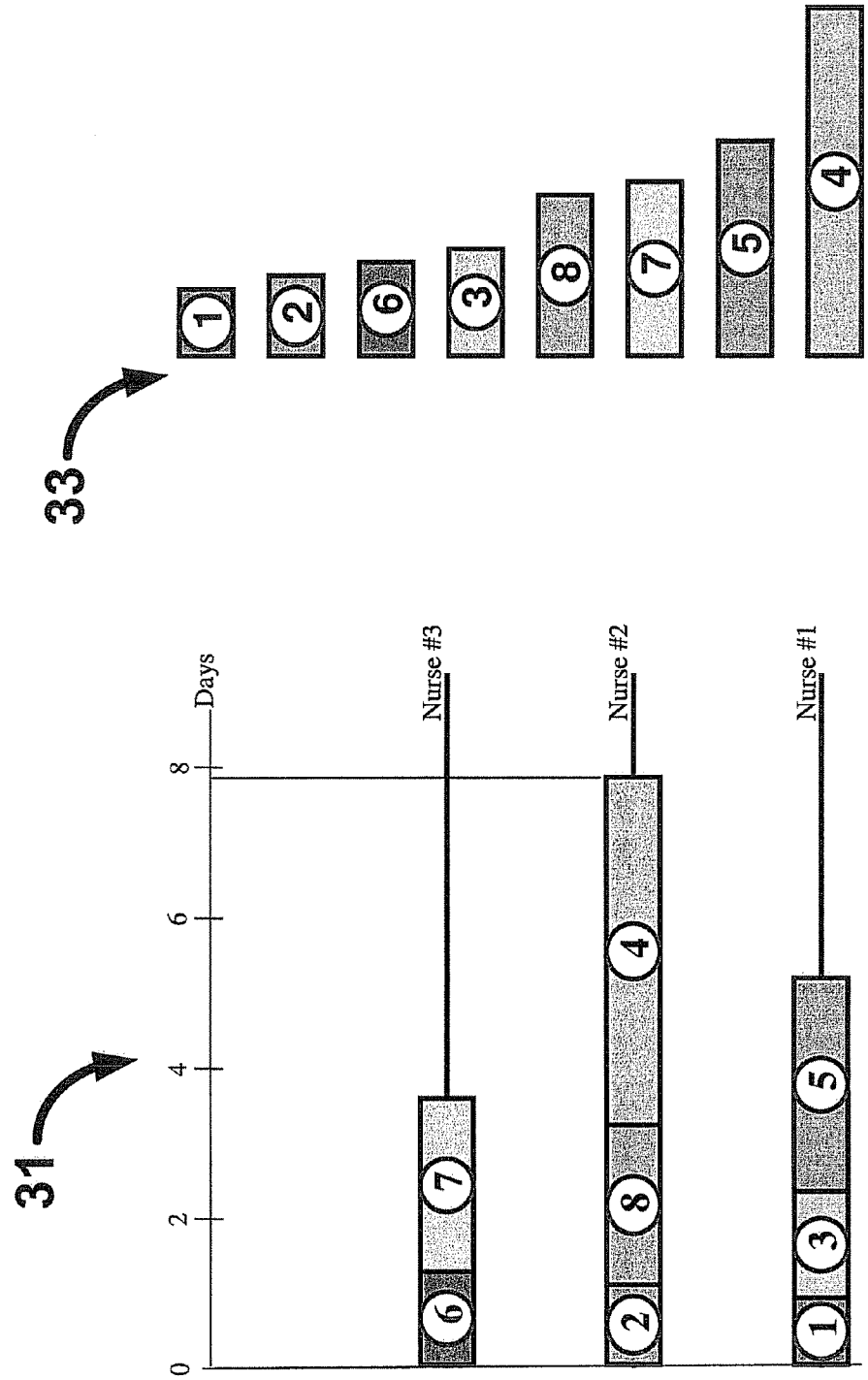
FIG. 3 is a diagram depicting the implementation of a shortest-processing-time first policy.

Another policy that may be implemented is referred to as shortest-processing-time (SPT) first. A shortest-processing-time first policy is implemented when the hospital desires to minimize the wait time metric. Wait time may be thought of as an intermediate storage of a job in the system due to lack of capacity. Thus, by reducing wait time, the hospital creates a larger capacity. FIG. 3 depicts the implementation of a shortest-processing-time first design parameter. A shortest-processing-time first policy sorts the jobs according to increasing processing times. Whenever a nurse finishes a job, the job with the shortest processing time at that instant is assigned to that nurse. Blocks 33 represent individual jobs and each job's relative processing time. According to the shortest-processing-time first design parameter, Nurse 1 will first process job 1, Nurse 2, job 2 and Nurse 3, job 6. Once Nurse 1 completes job 1, he will process the job with the least processing time, i.e. job 3. The process continues, as each nurse will take the job with the least processing time of the stack. The graph 31 on the left depicts a timeline for three nurses completing 8 jobs. As can be seen, the final job was not completely processed until day 8.

Figure 4:
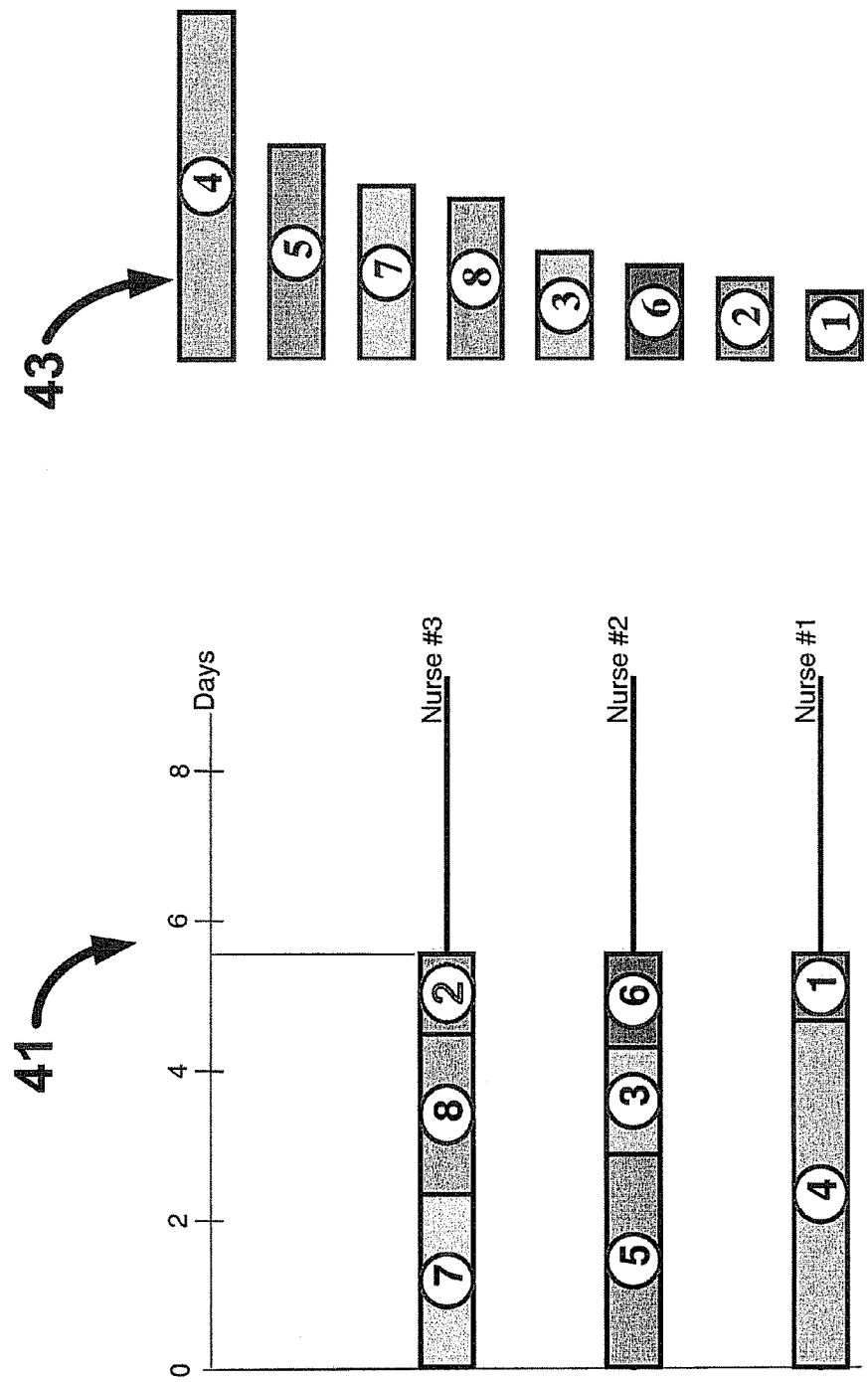
FIG. 4 is a diagram depicting the implementation of a longest-processing-time first policy.

Yet another policy that may be implemented is referred to as longest-processing-time (LPT) first. FIG. 4 depicts the implementation of a longest-processing-time first design parameter for the same set of eight jobs 33 depicted in FIG. 3. A longest-processing-time first policy may be implemented when a hospital desires to maximize throughput. In a longest-processing-time first policy, the jobs 33 are sorted in order of decreasing processing times. Whenever a nurse finishes a job, he will be assigned the job with the longest processing time. According to the timeline 41 of FIG. 4, Nurse 1 will first be assigned job 4, Nurse 2, job 5 and Nurse 3, job 7. Once, Nurse 3 finishes job 7, she will be assigned job 8, the job with the longest processing time at that instant. The process continues, as each nurse takes the job with the longest processing time of the stack.

As may be seen in the figure, all of the jobs will be processed before day 6. This is two days faster than that indicated in FIG. 3. However, jobs have to wait longer for the nurses to process them. For example, Jobs 1, 2 and 6 had to wait until day 4 for the nurses to process the jobs. Comparing FIGS. 3 and 4, it is observed that for identical jobs, a longest-processing-time first design parameter maximizes throughput at the expense of wait time. Conversely, a shortest-processing-time first design parameter minimizes wait time at the expense of throughput. Thus, the shortest-processing-time first and longest-processing-time first design parameters are negatively correlated. They may be thought of as couplers that couple the two functional requirements, raise throughput and reduce wait time, together.

Each of the design parameters discussed above, longest-processing-time first, shortest-processing-time first and earliest-due-date first may be used for optimizing a functional requirement. The result of implementing any of these design parameters is that none of them take into account the couplings among the functional requirements. Rather, each design parameter addresses only the specific corresponding functional requirement at the expense of other functional requirements. Thus, an understanding of the relationship or coupling between the design parameters is useful in resolving the couplings and optimizing the functional requirements to arrive at the claimed invention.

As discussed, raising throughput and reducing wait time are coupled because both are dependent on the same design parameter, i.e. the ordering and sequencing of processing time. Longest processing time, the design parameter which maximizes throughput, is actually the worst design parameter for reducing wait time. Conversely, shortest-processing-time first, the design parameter which minimizes wait time, is actually the worst design parameter for maximizing throughput. The coupling may be symbolically represented as:

$$\begin{Bmatrix} \text{raise throughput} \\ \text{reduce wait time} \end{Bmatrix} = \begin{bmatrix} X & X \\ X & X \end{bmatrix} \begin{Bmatrix} LPT \\ SPT \end{Bmatrix}$$

An element X in a matrix indicates that a design parameter has an effect on the functional requirement and an ○ indicates no effect on the functional requirement. From the matrix above, it is apparent that longest-processing-time first, the design parameter primarily responsible for raising the throughput, also affects reducing wait time. In other words, longest-processing-time first couples both raising throughput and reducing wait time. Similarly, shortest processing-time first couples both raising throughput and reducing wait time as well.

Deliver service on time is a third functional requirement. It is dependent not only on time to due date, but also on processing time as well. This is because a job with an early due date can still be completed and delivered on time if it has a short processing time. Thus, deliver service on time is affected not only by earliest due date first, but also by both the longest processing time first and the shortest processing time first. This coupling may be symbolically represented as:

$$\{\text{deliver service on time}\} = \{ X \quad X \quad X \} \begin{Bmatrix} LPT \\ SPT \\ EDD \end{Bmatrix}$$

Combining the two matrices above, the following is obtained:

$$\begin{Bmatrix} \text{raise throughput} \\ \text{reduce wait time} \\ \text{deliver service on time} \end{Bmatrix} = \begin{bmatrix} X & X & O \\ X & X & O \\ X & X & X \end{bmatrix} \begin{Bmatrix} LPT \\ SPT \\ EDD \end{Bmatrix}$$

This matrix represents the couplings, i.e., interdependencies, among three functional requirements in PAT, as indicated by the presence of an X in the off-diagonal elements. These couplings are resolved through redesign to arrive at the claimed invention.

Deliver service on time may be decoupled from raise throughput and reduce wait time by choosing slack time as the design variable and the least-slack-time first policy as the design parameter. The choice of slack time combines the time to due date and the processing time into a new variable so that the functional requirement, deliver service on time, becomes dependent solely on slack time.

Furthermore, a slack time dependent design parameter ensures consistency in on-time delivery because it serves as a buffer to absorb variability in processing time. A shorter slack indicates not only higher urgency to complete a job, but also a smaller margin of error for consistency in on-time delivery. Thus, applying the least-slack-time first design parameter to the health care delivery system will uncouple raising throughput and reducing wait time from maximizing consistency in on time delivery. The following representation depicts the partial resolution of the coupling.

$$\begin{Bmatrix} \text{raise throughput} \\ \text{reduce wait time} \\ \text{deliver service on time} \end{Bmatrix} = \begin{bmatrix} X & X & O \\ X & X & O \\ O & O & X \end{bmatrix} \begin{Bmatrix} LPT \\ SPT \\ LST \end{Bmatrix}$$

Figure 5:
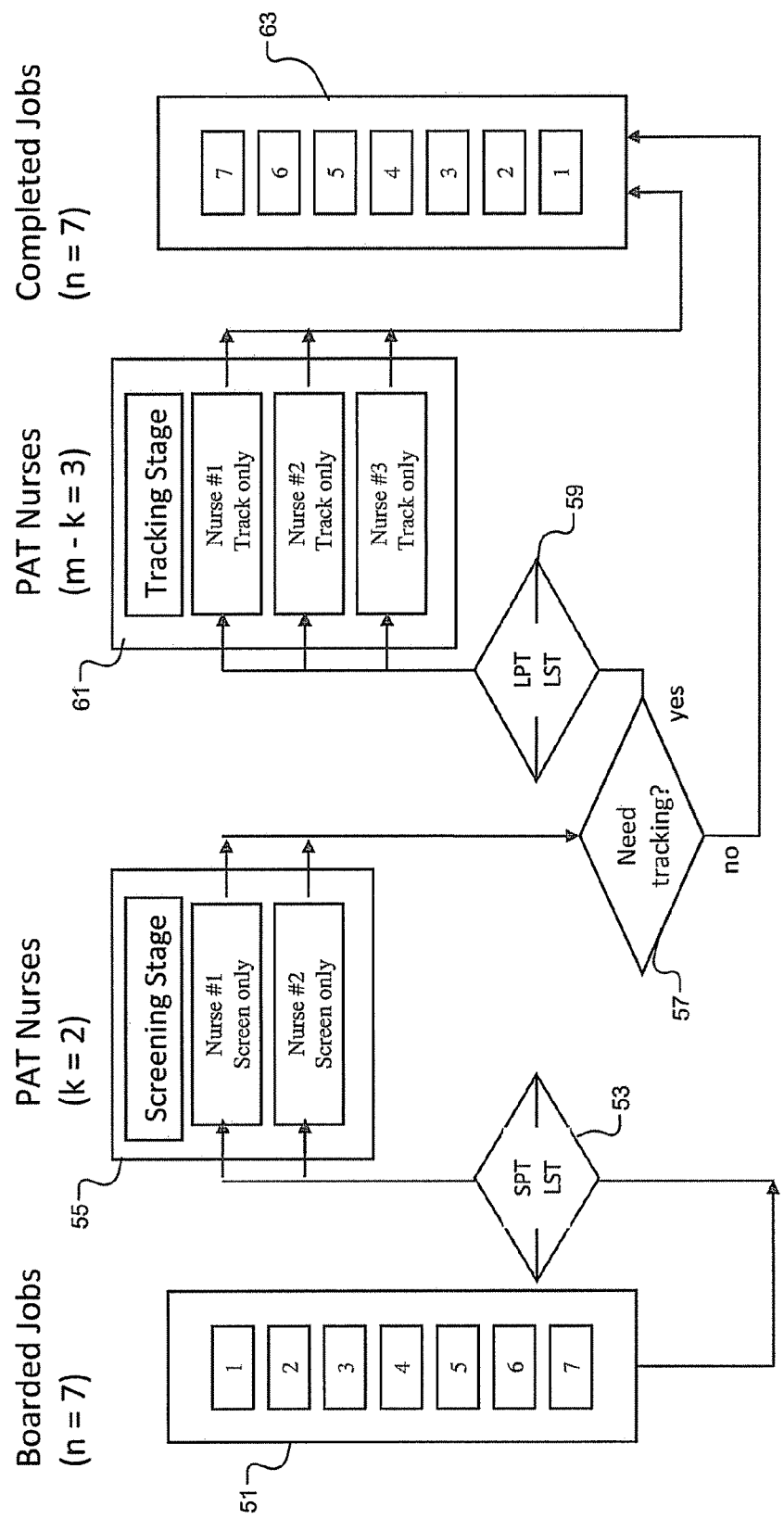
FIG. 5 is a flowchart depicting the healthcare management system being applied to a two-tiered pre-admissions testing unit.

As discussed, the remaining coupling of raising throughput and reducing waiting time exists because the respective design parameters, shortest-processing-time first and longest-processing-time first, are both dependent on processing time. Furthermore, the two design parameters contradict each other. To resolve this remaining coupling, a two-stage scheduler is chosen for PAT. As shown in FIG. 5, the PAT unit must finish n (n=7 in FIG. 5) jobs 51. To resolve the coupling problem discussed above, the PAT process is split into two stages, screening 55 and tracking 61. Similarly, m PAT nurses are split into two teams, screening nurses and tracking nurses. It is understood that the screening nurses and tracking nurses may be comprised of an entirely different nurses or the same group of nurses. The first stage, the screening stage 55, has k (k=2 in FIG. 5) of the m nurses in parallel performing the screening tasks only. The order of screening is chosen by the design parameters 53 which seek to reduce wait time and ensure on time delivery.

$$\begin{Bmatrix} \text{reduce wait time} \\ \text{deliver service on time} \end{Bmatrix} = \begin{bmatrix} X & O \\ O & X \end{bmatrix} \begin{Bmatrix} SPT \\ LST \end{Bmatrix}$$

The pre-procedure tests called for by the screening are then sent to the second stage for tracking 61 by the remaining m-k tracking nurses in parallel. The order of tracking is chosen by the design parameters 59 which seek to raise throughput and ensure consistency in on time delivery.

$$\begin{Bmatrix} \text{raise throughput} \\ \text{deliver service on time} \end{Bmatrix} = \begin{bmatrix} X & O \\ O & X \end{bmatrix} \begin{Bmatrix} LPT \\ LST \end{Bmatrix}$$

Of course, patients that need no tracking may be listed as completed 63 once a determination is made that tracking is not required 57. Thus, the replacement of the design parameter earliest-due-date first by the design parameter least-slack-time first and the implementation of the two-stage scheduler completely resolve the couplings, i.e., interdependencies, among the three functional requirements in PAT The foregoing design parameters may be applied to the health care delivery management system. FIG. 5 depicts an exemplary embodiment of the heath care delivery management system applied to the PAT process. It depicts a two-stage scheduler used in PAT unit. It is understood that a multi-stage scheduler may be implemented in other hospital or medical facility units, such as an ED, OR, and ICU and that the invention is not limited to application to PAT units or processes.

Figure 6:
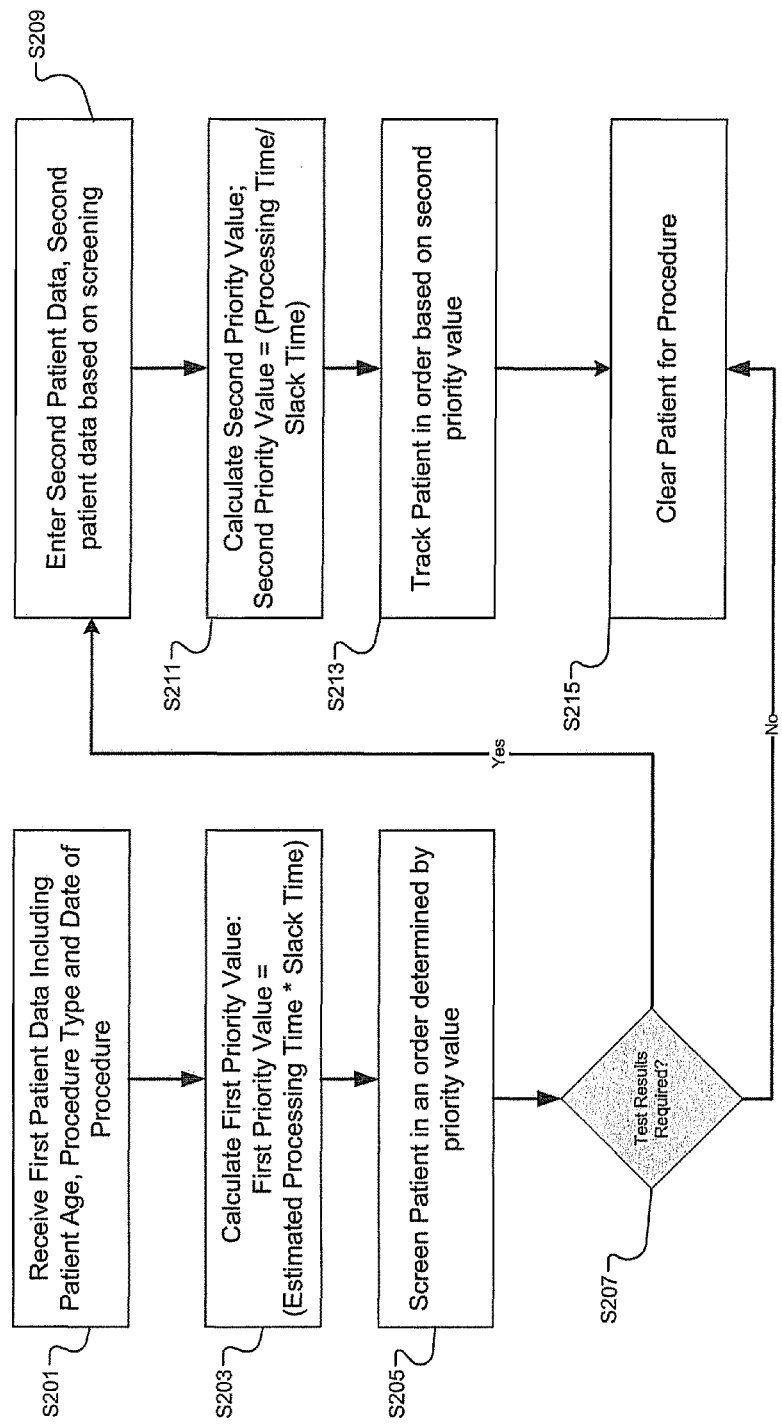
FIG. 6 is a diagram depicting an exemplary system level architecture of the health care management systems.

Referring now to FIG. 6, an exemplary method of managing healthcare delivery is described in greater detail. The method may be implemented on a single computer, or on multiple computers using client-server, parallel computing and/or hub and spoke computer models. A portion of the steps for carrying out the method may be represented in machine readable instructions residing on a computer readable medium.

Figure 7:
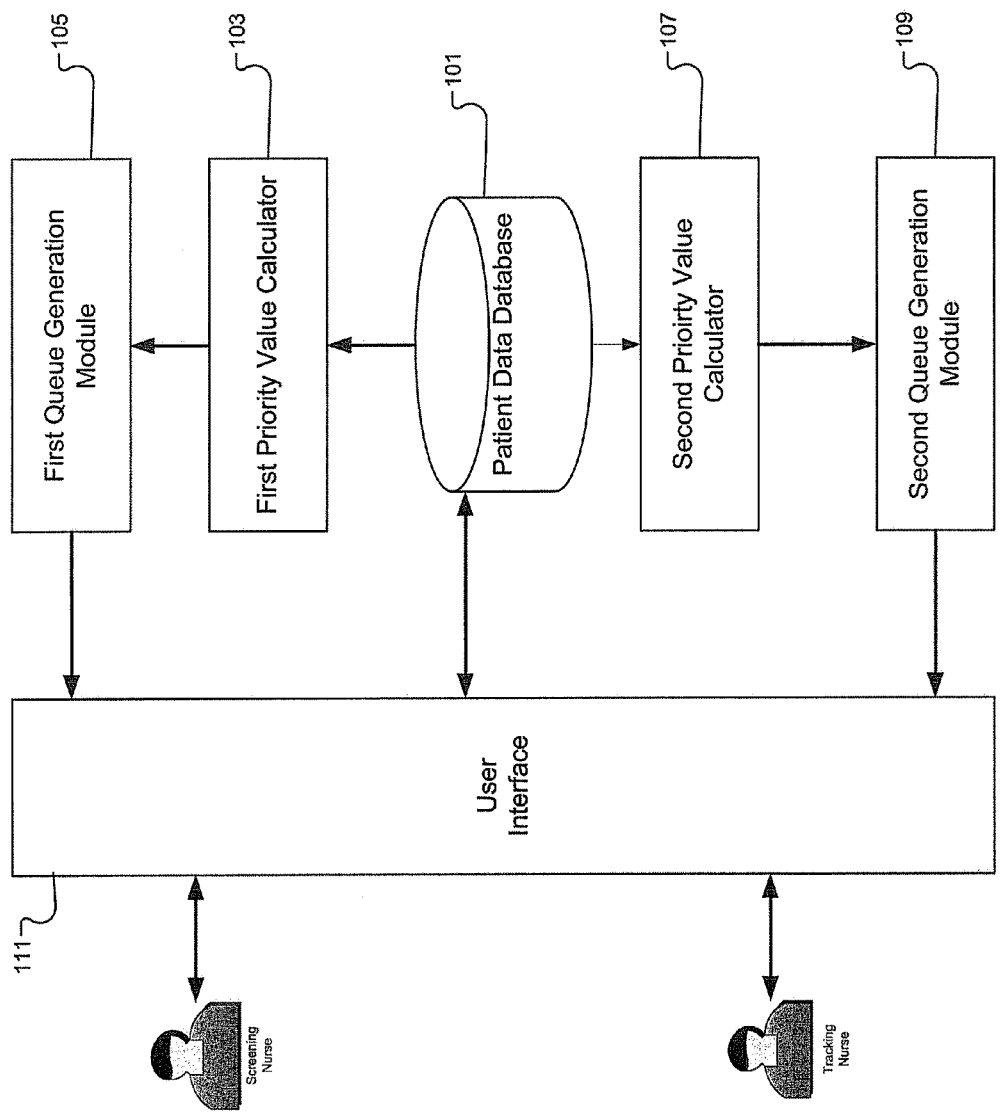
FIG. 7 is a flow chart depicting an exemplary method for managing healthcare delivery.

At step S201, patient data is received and may be stored to a data store 101, (as seen in FIG. 7), residing on the memory of a computer. As will be discussed below, patient data may be used to estimate the timeline of the "board-to-surgery" timeline. Exemplary patient data may include, but is not limited to the age of a patient, the type of procedure planned for the patient, the date of the procedure and whether or not the patient care is inpatient or outpatient. It is understood that for different units of a hospital, other types of patient data may be more relevant, such as health insurance provider, primary physician, etc. Patient data may be entered into the system when the patient is boarded by the healthcare provider or soon thereafter. This information may be obtained directly from the patient, a referring physician, the patient's medical charts or the hospital's records. Patient data is used to determine a priority value for the patient. The priority values are used to generate a screening queue, where patients are ordered in the queue based on their priority value.

At step S203, a queue position in a screening queue is determined for each patient using a design parameter that relates to the "board-to-surgery" timeline. A first priority value for each patient may be calculated for each patient using a hybrid of the shortest-processing-time first design parameter and the least-slack-time first design parameter. It is appreciated that hybrids of other design parameters may be alternatively implemented. As discussed, the first priority value may correspond to a queue position in the screening queue. At the screening stage, it may be advantageous to have the selected design parameter minimize wait time, which will result in increasing capacity. Furthermore, partially basing the selected design parameter on a least-slack-time first policy will maximize the consistency of on-time delivery. Thus, the matrices for the uncoupled sub-process may be expressed as:

$$\begin{Bmatrix} \text{reduce wait time} \\ \text{deliver service on time} \end{Bmatrix} = \begin{bmatrix} X & O \\ O & X \end{bmatrix} \begin{Bmatrix} SPT^{est} \\ LST^{est} \end{Bmatrix}$$

Note that in the design parameter vector above, the shortest-processing-time first and the least-slack-time first are estimates. This is because at the time of screening, the processing time is unknown. Estimating the processing times for each patient at the screening process, however, will still capture the primary intent of the selected design parameters. This information may be derived from historical or empirical data on processing time of patients. Furthermore, every time a patient is screened, statistical data relating to the patients age, procedure and processing time, may be entered into the empirical data. Alternatively, a hospital administrator or consultant may assign processing times to certain groups.

The primary intents of the first stage of PAT process are to capture two categories of patients, i.e., jobs: (1) jobs that need no pre-procedure testing and, therefore, require no tracking; and (2) jobs that have short slack time, so that they may be sent quickly to the tracking stage for immediate tracking. Historical data suggests that jobs that require screening but no pre-procedure testing take approximately 1.33 days to process. The corresponding slack time for these jobs is (TDD−1.33) wherein TDD is Time To Due Date. It is noted, however, that the number 1.33 days is an estimate and may be chosen either by the designer of the system or by the hospital staff. Furthermore, as the system is used, this number may be gradually updated through use of learned data. Also, in the exemplary embodiment times are represented in days, but it is appreciated that time may be represented in hours, minutes, seconds or years. For jobs that need several pre-procedure testing and are suspected of having a short slack time, the slack time is assigned the value 1 day. The processing time for these jobs is then (TDD−1). For all other jobs, the average of the two estimates above is used. That is: for the processing time, (TDD+0.33)/2; for the slack time, (TDD−0.33)/2. It is noted, however, that estimating processing time may be implemented differently so long as jobs suspected of needing no pre-procedure testing are assigned a short processing time estimate and jobs that need several pre-procedure testing and suspected of having short slack time are assigned a long processing time estimate.

Since reducing wait time calls for the shortest-processing-time first; and consistently delivering service on time calls for the least-slack-time first, a priority value may be expressed as the combination of the two design parameters: Priority Value=Processing Time*Slack Time with the policy of processing smallest-priority-value first. It is noted that other combinations may be implemented by the system designer. The foregoing is merely one exemplary combination of the design parameters. The following table represents one way that priority value may be calculated by the system:

| Category | Processing Time | Slack Time | Priority Value |
|---|---|---|---|
| Job needs no pre-procedure tests | 1.33 | TDD − 1.33 | 1.33 * (TDD − 1.33) |
| Job needs many pre-procedure tests | TDD − 1 | 1 | TDD − 1 |
| Otherwise, average of the two above | (TDD + 0.33)/2 | (TDD − 0.33)/2 | (TDD + 0.33) * (TDD − 0.33)/4 |

Based on a patient's patient data, the system must choose which of the three categories to apply to each patient. Again, historical data may be used to assign categories to patients. Also, hospital policies, intuitive assignment by administrators, or other means of assigning a category may be used. In this exemplary embodiment historical data is used. All jobs with a zero count, that is jobs that require no pre-procedure tests, involve outpatient care. Further, if a patient is undergoing an outpatient procedure and is under the age of 50, there is a 73% probability that the count is a zero count. Jobs with a count greater than or equal to four, i.e. patients requiring four or more pre-admission tests, will typically have little slack time. The majority of these jobs involve inpatient care, and more specifically, orthopedic or vascular surgery. Thus, one possible embodiment of the system may be designed to assign the following priority values to the following set of patients:

1.33(TDD−1.33) if patient care is outpatient and age<50;
TDD−1 if patient care is inpatient and surgery is either orthopedic or vascular; and
(TDD+0.33)*(TDD−0.33)/4 otherwise.

After assigning a patient to a priority value category, a first priority value corresponding to the patient is calculated by the system. At step S205, the screening nurses will then process jobs having the lowest priority value first. The priority values may be displayed in the form of a queue, generated by a queue generation module 105, FIG. 7. The priority values may be displayed on a display unit such as an LCD monitor, a TV screen, or any other type of display. Alternatively, the priority values may be sent to the nurses over a communications network. For example, the nurse may receive the results via email or cell phone. The patients may be ranked in a queue by order of priority value. Alternatively, a daily schedule may be generated based on estimated screening times and priority values.

At step S205 the screening nurses will screen the patients by contacting them over the telephone, or other means of communication. The patient will answer questions regarding their medical status and history. The nurse will receive the patient's answers and may input the patient's answers, in the form of patient tracking data, into the system via a user interface on a computer. The patient tracking data may be stored in a data store. Based on the patient's answers, one or more of a nurse, a doctor, or the system may choose the required pre-procedure tests. The required pre-procedure tests are also stored as patient tracking data. At step S207, if it is determined that no pre-procedure test is needed, the patient is then cleared for the procedure.

At step S209 a queue position in a tracking queue may be calculated based on the patient data and patient tracking data. A second priority value may be calculated to indicate a queue position in the tracking queue. The tracking queue ranks or schedules the tracking jobs. In the tracking phase of PAT, it is beneficial to raise the throughput and consistently deliver the service on time. The corresponding design parameters to achieve these functional requirements are the longest-processing-time first and the least-slack-time first; as expressed in the following matrices for the uncoupled sub-process:

$$\left\{\begin{array}{c}\text{raise throughput}\\\text{deliver service on time}\end{array}\right\} = \begin{bmatrix} X & O \\ O & X \end{bmatrix}\left\{\begin{array}{c} LPT \\ LST \end{array}\right\}$$

Note that the design parameters no longer need to be based on estimated values. After the screening process, the required tests will be known, and the average processing time for obtaining each test result is known. Since raising throughput calls for the longest-processing-time first; and delivering service on time consistently calls for the least-slack-time first, a second priority value may be expressed as the ratio of the two design parameters: Priority Value=Processing Time/Slack Time; with the policy of processing the largest-priority-value first. The processing times for each type of test may reside in a data structure in memory or may be entered by the nurse. The time to due date can be calculated from the patient data, as it is the date of the procedure—the actual date. The slack time equals to time to due date less processing time can be calculated as well. At step S211, the priority values are calculated and a tracking queue may be generated by the system.

At step S213, the tracking nurses will then process jobs having the highest priority value first. As mentioned, the patients may be ranked in a queue by order of priority value. Alternatively, a daily schedule may be generated based on estimated screening times and priority values. The priority values, the tracking queue, or a schedule may be displayed on a display unit such as an LCD monitor, a TV screen, or any other type of display. Alternatively, the priority values, the tracking queue, or a schedule may be sent to the nurses over a communications network. For example, the nurse may receive the results via email or cell phone.

It is noted that the ratio may be expressed in another form. For example, the second priority value may be expressed as Slack Time/Processing time. In this case, the lowest priority value would be processed first, as it would be the most urgent.

Once a tracking nurse begins tracking a patient, the tracking nurse can input what portions of the tracking are complete. This type of input will update the patient tracking data and will effect the processing time. Once this occurs, the second priority value may be recalculated for the patient.

Once the tracking is complete at step S215, the patient may be cleared for the planned surgical procedure.

FIG. 7 depicts a system implementing the foregoing method for managing healthcare delivery. The steps shown in FIG. 6 generally correspond to the components of the system shown in FIG. 7.

For exemplary purposes, another system is described with respect to central sterilization (CS) process for surgical instruments in a hospital. The CS process is a critical step in the healthcare delivery as the process ensures that surgical or medical equipment is sterile at the time the equipment comes in contact with the patient, e.g. at the time of an examination or surgery. The central sterilization inventory and services represent a significant cost center for a hospital.

The CS process for a particular surgical set of instruments is activated when a patient is boarded for a procedure. The procedure requires surgical instruments in sets to be made available at the time of surgery. FIG. 8 represents an exemplary surgery schedule and the corresponding required surgical instrument sets. As may be seen from the figure, the schedule may include a patient board date 131, the due date of the surgery 141, a procedure code indicating the type of surgical or medical process 133, a list of instrument sets called for by the procedure 135, the set ID # for each set 137, and a description of the sets 139.

Figure 9:
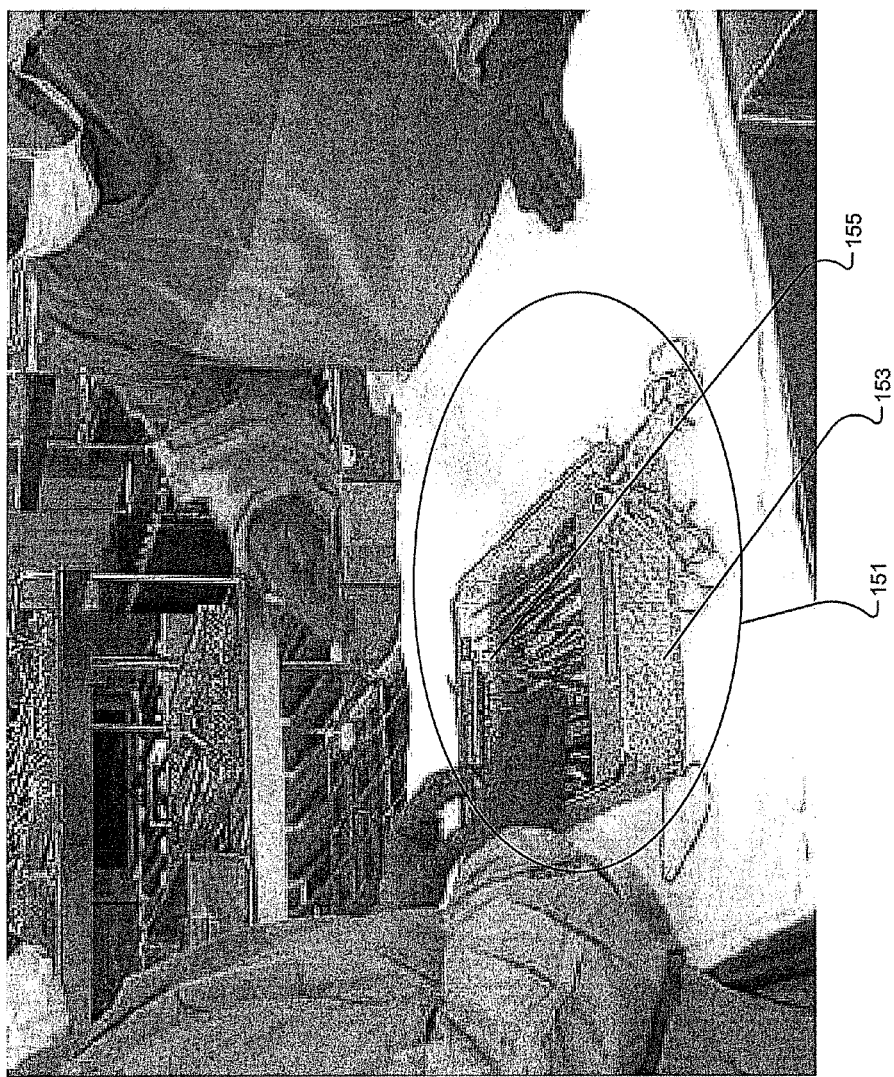
FIG. 9 is a photograph showing an exemplary instrument set.

A typical set consists of several instruments in a tray or pack as shown in FIG. 9. A set 151 may include a tray 153 and instruments 155. Typically, a request for an instrument set is entered into the inventory system to register a demand against the inventory reserve for the scheduled date and time of surgery. On the day of surgery, the requested sets of instruments 151 are brought in trays 153 or packs (not shown) out of the sterile storage area to the operating room. Once used up and soiled, the instrument 155 and trays 153 are carted to the CS department to begin the CS process of decontamination, packaging and sterilization of the instrument set for re-use.

Figure 10:
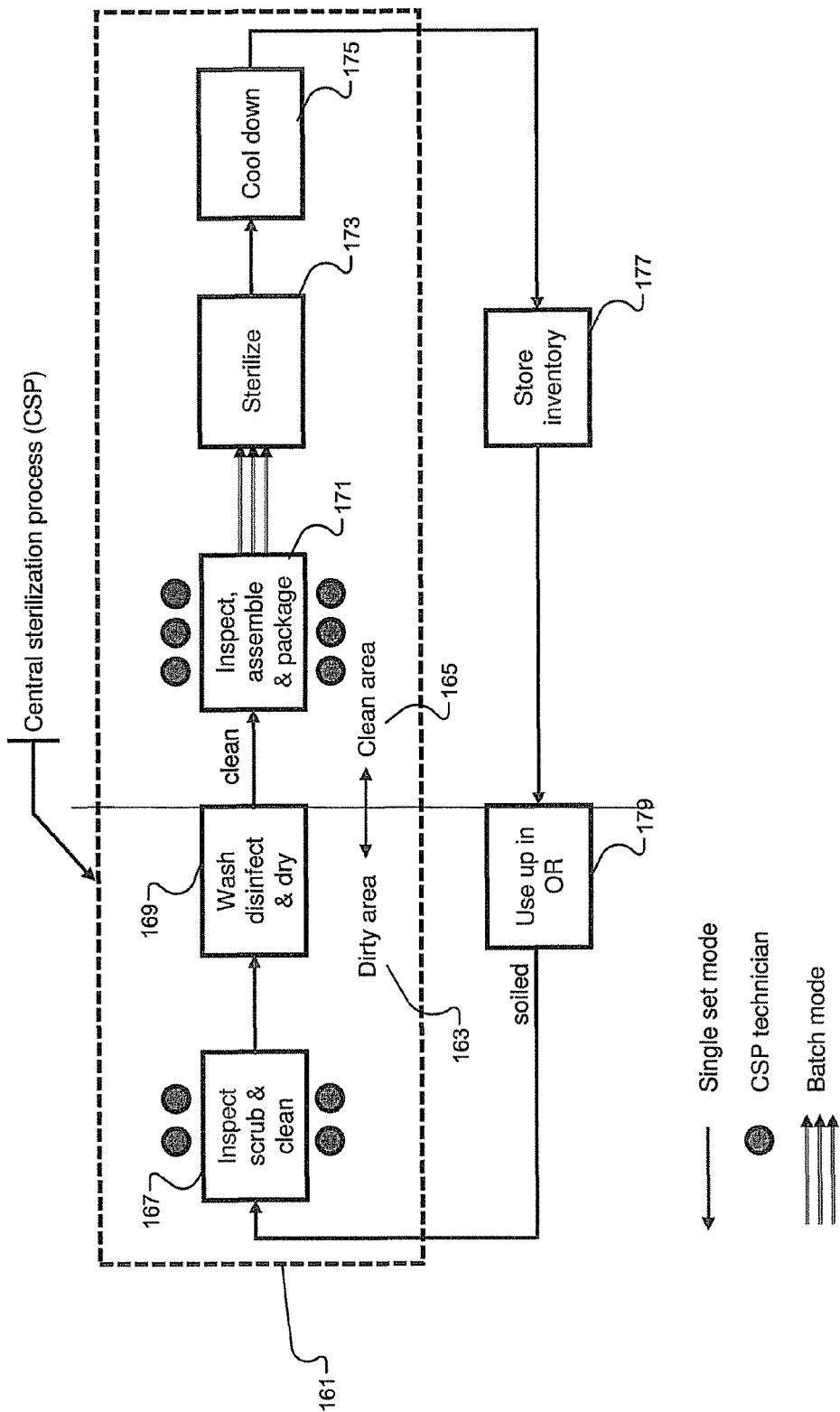
FIG. 10 is a diagram showing the steps in the central sterilization process.

FIG. 10 depicts the events that must be completed during the CS process and the corresponding areas where the events occur. As can be seen, the CS department has a dirty area 163 and a clean area 165. In dirty area 163, the instruments are inspected scrubbed and cleaned 167 as well as washed disinfected and dried 169. In the "dirty" decontamination area 163, the CS technicians manually scrub, clean, function test and inspect the instruments for any missing piece 167. The instruments and trays are then washed, disinfected and dried in the washer 169. Once dried, the decontamination is complete and the instruments and trays are safe for handling. They are transported to the "clean" assembly area 165 where the CS technicians inspect the instruments once more for completeness and package them into sets of trays or packs as called for by a procedure 171. Multiple sets are placed onto a sterilization cart and loaded in batch into the sterilizer for sterilization 173. On completion, the cart is removed from sterilizer and sets are allowed to cool down 175. Sterile sets are then transported to the sterile area for storage 177. The inventory is updated to reflect the replenishment of the sets so that they the instruments may be used again 179. This completes the CS process.

A primary functional requirement of the CS process is to deliver the instrument sets on time for the surgical procedure. While the efficiency with which to attain the functional requirement is dependent on the efficiency of the sub-processes that comprise the CS process, it is also dependent on effective scheduling; i.e. the order and sequence by which each set is processed through the sub-processes. Most hospitals employ the first-come-first-served policy to process the sets. This policy fails to recognize the conditions for on-time delivery. By recognizing the conditions, the scheduling corresponding to the CS process may be optimized through implementation of the claimed invention.

There are three conditions to consider for on-time delivery of instrument sets. They are: (1) inventory reserve does not run out; and if it does run out, (2) there is time to process a set in time for the procedure. If none of the two conditions exist, then (3) a loaner must be made available. The existence of these three conditions is a function of three variables associated with a set. The first variable is the processing time $P_k$ for the set k. $P_k$ is the sum totals of the processing time of the sub-processes that comprise the CS process 167-175. The value of value $P_k$ may be estimated from historical data or may be derived by experts. Furthermore, as the system continuously runs, machine learning algorithms and data mining algorithms may be implemented to obtain better estimates. The second variable is $D_k$, the time remaining until the set k will be required by a procedure. The value of this variable is typically known because the procedures are typically scheduled well in advance. The third variable is $T_k$, the time to when the inventory for set k runs out. In spite of the fluctuating demand and replenishment, the value of $T_k$ can be estimated by tracking the inventory as a function of demand and replenishment. Namely, inventory $I_k(t)$ of a set k at any time t is the reserve inventor $S_k$ minus accumulation of demand $D_k$ and replenishment $R_k$ up to the time t:

$$I_k(t) = S_k - \Sigma D_k(t) + \Sigma R_k(t)$$

The time to when the inventory goes critical, i.e. zero, is $T_k$. It is the solution to the equation:

$$S_k \Sigma D_k(T_k) + \Sigma R_k(T_k) = 0.$$

Figure 11:
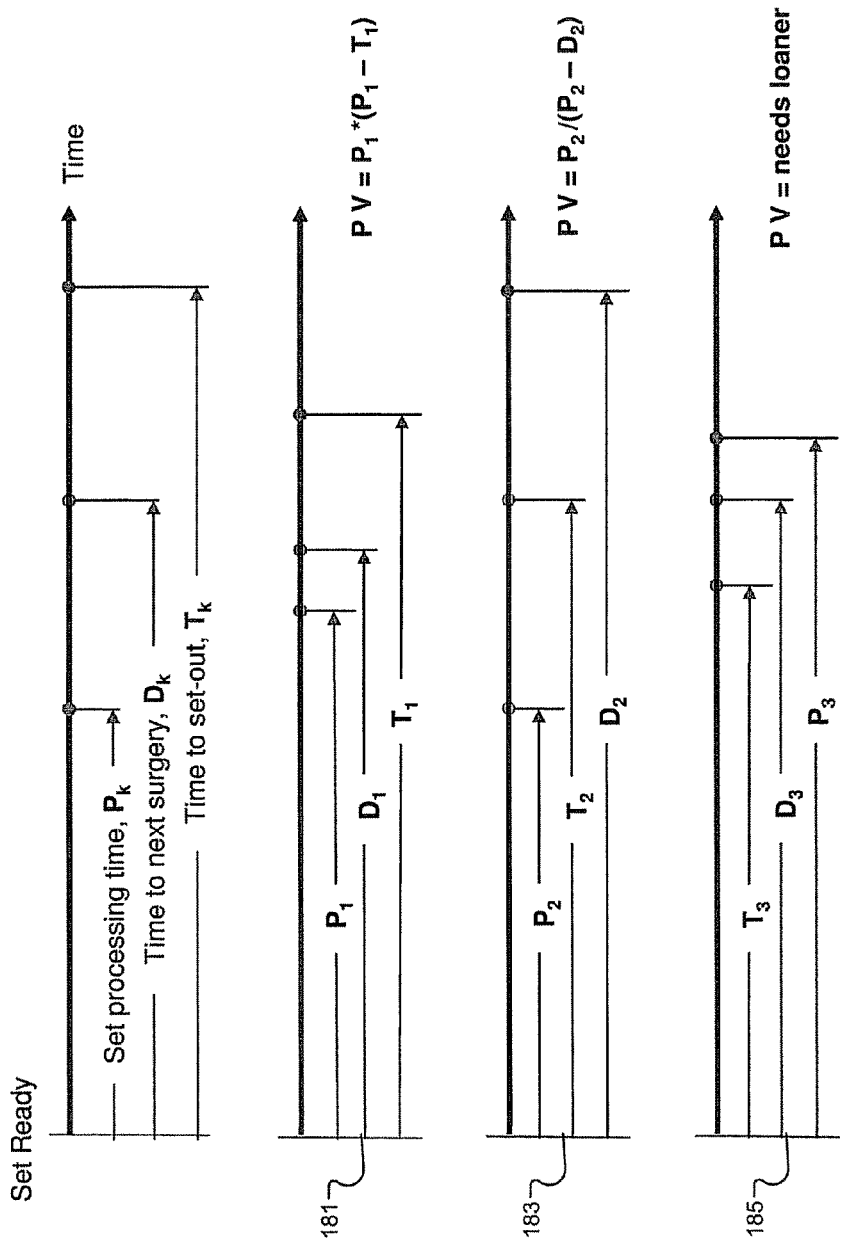
FIG. 11 is a diagram depicting the timelines of various conditions or scenarios that may occur when processing surgical sets.

FIG. 11 illustrates a series of timelines for various scenarios for demand of an instrument set. Given the values of the three variables associated with a set k, the relative positions of the variables along the timelines determine the condition the set is in the CS process. Depending on the condition the set is in, a priority value is assigned to the set. Similar to as was discussed in the previous embodiment, the priority values are used to determine a schedule for processing the instruments.

For example, condition (1) exists in timeline 181 when $T_k$ is greater than $D_k$. Namely, the inventory is available to cover the next call for set k by a procedure. Under this condition, scheduling efforts should focus on building up the inventory reserve. The functional requirements for these efforts are to reduce in-process inventory and to deliver the set in time to cover zero inventory at time $T_k$. As discussed previously, the corresponding design parameters are SPT, the smallest-processing-time $P_k$ first policy and LST, the least-slack-time ($T_k - P_k$) first policy:

$$\left\{ \begin{array}{c} \text{reduce in-process inventory} \\ \text{deliver set on time at } T_k \end{array} \right\} = \begin{bmatrix} X & O \\ O & X \end{bmatrix} \left\{ \begin{array}{c} SPT \\ LST \end{array} \right\};$$

The priority value PV for scheduling the sets under this condition may be represented as:

$$PV = P_k * (T_k - P_k);$$

In this scenario, the sets having the smaller the priority value should be processed first.

Additionally, in building batches of instrument sets for sterilization in batch at the sterilizer, n CS technicians should work jointly to build batch sequentially; instead of working separately to build n parallel batches. The former is more efficient in reducing in-process inventory, consistent with the focus in Condition (1).

Condition (2) exists in timeline 183 when $T_k$ is less than $D_k$. Namely, the inventory is not able to cover the next call for set k by a procedure. Under this condition, scheduling efforts should focus on delivering the set on time to meet the next call for set k at time $D_k$. The functional requirements for these efforts are to raise throughput and to deliver set on time at $D_k$. The corresponding design parameters are LPT, the longest process time, $P_k$, first policy and LST, the least slack time, $(D_k - P_k)$, first policy:

$$\left\{ \begin{array}{c} \text{raise throughput} \\ \text{deliver set on time at } D_k \end{array} \right\} = \begin{bmatrix} X & O \\ O & X \end{bmatrix} \left\{ \begin{array}{c} LPT \\ LST \end{array} \right\}$$

The priority value PV for scheduling the sets under this condition may be represented as:

$$PV = P_k / (D_k - P_k)$$

In condition (2), the sets having larger priority values are processed first. It should be appreciated that this, or any of the other disclosed priority value equations, may be expressed in alternative ways. For example, the equation provided for condition (2) may be expressed by $PV = (D_k - P_k) / P_k$, so that the sets having the smallest priority values are processed first. It should be further appreciated that any of the equations provided in this disclosure may be expressed in various ways so long as the spirit of the selected design parameters is adhered to.

Condition (3) exists in timeline 185, when $P_k$ is greater than the maximum of $(D_k, T_k)$. When condition (3) exists, neither inventory reserves nor optimal processing of the current set k can cover the next call for set k by a procedure. The only recourse is to procure a loaner or to purchase more inventories. The $(D_k, T_k)$ values of the current set k is then updated to reflect the addition of the loaner. The set is then re-scheduled per condition (1) if $T_k$ is greater than $D_k$ and condition (2) if $T_k$ is less than $D_k$.

Given the values $P_k$, $D_k$ and $T_k$ of a set, the set can be classified into one of the three groups that correspond to the three conditions a set is in. In Group (3) may be comprised of the sets satisfying Condition (3). Group (3) should be processed first because loaner sets have to be arranged with other suppliers, e.g. nearby hospitals or clinics. Group (2) consists of sets satisfying Condition (2), that is—sets running out of inventory. Group (2) is processed after Group (3). Group (1) consists of the sets satisfying Condition (1). As Group (1) is primarily processed to raise inventory levels, Group (1) should be processed last. Within a group, the members are processed according to their priority values, i.e. the larger the priority value, the higher the priority for Group (2); the smaller the priority value, the higher the priority for Group (1).

Figure 12:
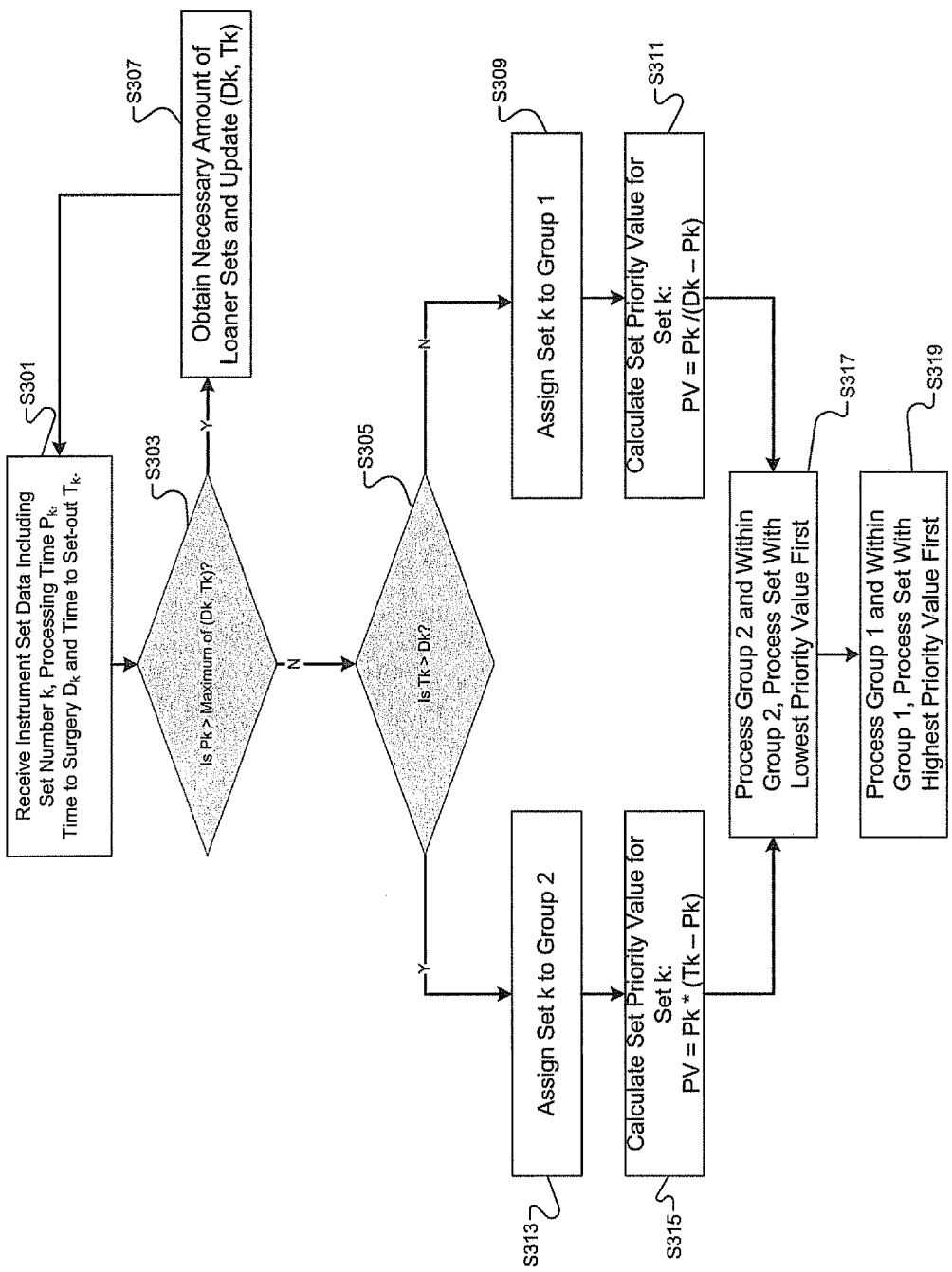
FIG. 12 is a flow diagram of an exemplary method for processing surgical sets.

A method for processing inventory sets in a CS is now described in greater detail. FIG. 12 depicts an exemplary embodiment of the method. It should be appreciated that the steps provided do not need to be performed in this particular order, and the order provided is exemplary in nature. For exemplary purposes, a hospital may have n different sets, each set having its own set ID number. Each set ID number will have a corresponding inventory. Within each set, there is a unique set of instruments for a particular purpose. For example, a set for suturing may have a needle holder, 1 scissors, 1 forceps, 1 hemostat, all in 1 tray. This tray would have a unique ID number. As may be appreciated, the instruments are generally reusable, but the set may contain disposable items. Once used and soiled, the reusable instruments must be decontaminated, packaged and sterilized for re-use. The sealed sterile pack comprises one inventory of the particular set.

At step S301, the system, which may be embodied as various modules running on a single computer or a plurality of computers, receives set data for one or more sets. The set data can include the processing time for the set ($P_k$), the time to surgery ($D_k$) and the time to set out ($T_k$). As discussed, processing time of a set represents the amount of time required to get the set thru the sub-processes and into the inventory storage. The time to surgery represents the amount of time until the particular set will be needed for a procedure. This is a known variable since surgery is scheduled when the patient is boarded. The time to set-out is the amount of time until the inventory will be depleted. As discussed earlier, this may be determined by solving for $T_k$ in the equation: $S_k - \Sigma D_k(T_k) + \Sigma R_k(T_k) = 0$.

At steps S303 and S305, the logic for assigning a set to a group is performed. First, the processing time is analyzed to determine if a loaner set will be required. If the processing time exceeds the amount of time until the surgery and the amount of time until set out, then a loaner may be required and the hospital may begin the process to obtain a loaner set at S307. On the other hand, if the processing time is less than either of these values, then the system will analyze the amount of time until the surgery and the amount of time until set out at S305. If the time to surgery is greater than the time to set out, then the set is assigned to group 2 at S309. At S311, the priority value for the set is calculated using, for example, $PV = P_k / (D_k - P_k)$. If time to set out exceeds time to surgery, then the set is assigned to group 1 at S313. At S315, the priority value for the set is calculated using, for example, $PV = P_k * (T_k - P_k)$.

Once all of the sets or a portion of the sets are assigned groups and priority values, then the CS workers may begin processing the instruments and reassembling the packs, that is once steps 301-315 are performed for multiple sets. It should be appreciated that steps S301-S315 should be run on a computer system. Said computer system may be run weekly, daily, hourly, or continuously, depending on the throughput of the healthcare facility. Hospitals having hundreds of procedures done on a daily basis will likely benefit from running the system continuously. Clinics that do procedures on certain days of the week will likely only need to run the system once a week.

After completion of steps S301-S315, the CS workers may process Group (2) at step S317. When processing Group (2) with priority values using the given formulas, the set with the highest priority value is processed first. At step S319, Group (1) is processed. When processing Group (1) with priority values using the given formulas, the set with the lowest priority value is processed first. As previously discussed, it should be appreciated that if the formulas are manipulated, then the effect of a priority value may be reversed, e.g. process the set with the lowest priority value first instead of last.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for managing healthcare delivery comprising:
   receiving patient data for two or more patients scheduled for a medical procedure, where a timeline for the medical procedure is in part derived from the patient data;
   determining, using a computer processor, a queue position in a screening queue for each patient using a first design parameter associated with the timeline for the medical procedure, where the screening queue indicates the order in which a screening process is administered to each patient, and wherein the first design parameter combines a shortest processing time design parameter and a least slack time design parameter;
   screening the patients in accordance with the screening queue;
   determining for patients having completed the screening process medical testing required for the medical procedure based on information obtained during the screening process;
   determining, using a computer processor, a queue position in a tracking queue for patients having completed the screening process using a second design parameter that is negatively correlated to the first design parameter and associated with the timeline for the medical procedure, where the tracking queue indicates the order in which patients are contacted to determine status of medical testing required for the medical procedure, wherein the second design parameter combines a longest processing time design parameter and the least-slack-time design parameter, and wherein a processing time of a patient corresponds to an amount of time to complete the screening process and the tracking process for the patient and wherein a slack time of the patient corresponds to the difference between an amount of time until the medical procedure is to be performed and the processing time,
   and wherein the first and second design parameters are negatively correlated such that the first design parameter is defined by a direct relationship between the processing time of a patient and the slack time of the patient, and the second design parameter is defined by an inverse relationship between the processing time of the patient and the slack time of the patient; and
   tracking the medical testing required for each patient having completed the screening process in accordance with the tracking queue.

2. The method of claim 1 wherein the first design parameter associated with the timeline for the medical procedure minimizes wait time for the two or more patients, wherein wait time is an amount of time corresponding to a patient being scheduled for the medical procedure and commencement of the screening time.

3. The method of claim 2 wherein processing time of a patient corresponds to an amount of time to complete the screening process and the tracking process for the patient and wherein slack time corresponds to the difference between amount of time until the medical procedure and the processing time.

4. The method of claim 2 further comprising calculating a first priority value of the patient based on the product of an estimate of the processing time and an estimate of the slack time, wherein the first priority value is used to determine the queue position in the screening queue for each patient.

5. The method of claim 1 wherein the second design parameter that is negatively correlated to the first design parameter and associated with the timeline increases throughput for the two or more patients, wherein throughput corresponds to an amount of patients tracked in a period of time.

6. The method of claim 5 further comprising calculating a second priority value of the patients based on the ratio between the processing time and the slack time, wherein the second priority value is used to determine the queue position for each patient in the tracking queue.

7. The method of claim 1 further comprising clearing a patient for the medical procedure upon determining the status of the medical tests required is complete.

8. The method of claim 1 wherein the patient data for each patient includes an age corresponding to the patient, a type of medical procedure corresponding to the patient, and a date corresponding to the medical procedure corresponding to the patient.

9. The method of claim 1 wherein the patient data is used to estimate processing time and slack time.

10. The method of claim 1 further comprising clearing one of the two or more patients for the medical procedure upon completion of the tracking process for the patient.

11. A method for managing healthcare delivery comprising:
    receiving patient data for a patient, wherein the patient data includes age of the patient, a procedure corresponding to the patient, and a date corresponding to the procedure;
    determining, using a computer processor, first priority values for a plurality of patients, wherein a first priority value of the patient is based on the patient data and a product of an estimate of a processing time and a slack time of the patient, wherein processing time is an amount of time required to complete the screening and the tracking and slack time is a difference between an amount of time until the date of the procedure and the estimate of the processing time, and wherein the first priority values indicate queue positions in a screening queue;
    screening the patient in accordance with the screening queue, wherein screening relates to obtaining patient tracking data relating to at least one of the medical history of the patient and the diagnosed conditions of the patient;
    receiving patient tracking data;
    determining, using a computer processor, second priority values for patients having completed the screening process, wherein a second priority value of the patient is based on the patient tracking data of the patient, the patient data of the patient, and a ratio between the processing time of the patient and the slack time of the patient, and wherein the second priority values indicate queue positions in a tracking queue;

tracking the patients having completed the screening process in accordance with the tracking queue, wherein tracking includes obtaining results of medical tests required for the procedures corresponding to the patients, and wherein the first and second priority values are negatively correlated such that the first priority value is defined by a direct relationship between the processing time of a patient and the slack time of the patient, and the second priority value is defined by an inverse relationship between the processing time of the patient and the slack time of the patient.

12. The method of claim 11, wherein screening includes receiving the patient tracking data, and wherein the patient tracking data determines the medical tests required to clear a patient for the procedure.

13. The method of claim 11, wherein tracking includes obtaining results to the medical tests required before clearing a patient for a procedure.

14. The method of claim 11, wherein the estimated processing time is based on historical data relating to processing times of previous patients having a similar age as the patient and undergoing the same procedure as the patient.

15. The method of claim 11, further comprising updating the patient tracking data and the processing time when at least a portion of the results of the medical test required are obtained.

16. The method of claim 15 further comprising determining the second priority value upon updating the processing time.

17. The method of claim 11 further comprising generating a schedule for completing the screening based on the first priority values.

18. The method of claim 11 further comprising generating a schedule for completing the tracking based on the second priority values.

19. A system for managing healthcare delivery, the system being embodied as computer readable instructions stored on a non-transitory computer readable medium, the system comprising:
a data store storing patient data relating to a patient, wherein the first patient data includes age of the patient, a procedure corresponding to the patient, and a date corresponding to the procedure;
a first calculation module calculating a first priority value for the patient, wherein the first priority value is based on the patient data and a product of an estimate of a processing time and a slack time of the patient, wherein processing time is an amount of time required to complete the screening and the tracking and slack time is a difference between an amount of time until the date of the procedure and the estimate of the processing time, and wherein the first priority value relates to a queue position in a screening queue, and wherein screening includes obtaining patient tracking data of the patient;
the data store storing the patient tracking data, wherein patient tracking data includes at least one of a medical history of the patient and diagnosed conditions of the patient; and
a second calculation module calculating a second priority value for the patient, wherein the second priority value is based on the patient tracking data of the patient, and a ratio between the processing time of the patient and the slack time of the patient, and wherein the second priority value indicates a queue position in a tracking queue, wherein tracking is obtaining medical tests required for clearing the patient for the procedure corresponding to the patient, and wherein the first and second priority values are negatively correlated such that the first priority value is defined by a direct relationship between the processing time of a patient and the slack time of the patient, and the second priority value is defined by an inverse relationship between the processing time of the patient and the slack time of the patient.

20. The system of claim 19, wherein the screening includes receiving the patient tracking data, and wherein the patient tracking data determines the medical tests required to clear the patient for the procedure.

21. The system of claim 19, wherein tracking includes ensuring the medical tests required are received before clearing the patient for the procedure.

22. The system of claim 19, wherein the estimated processing time is based on historical data relating to processing times of previous patients having similar patient data as the patient.

23. The system of claim 19, further comprising an update module updating the patient tracking data and the processing time when at least a portion of the medical test required are obtained.

24. The system of claim 22, wherein the second calculation module determines the second priority value upon updating the processing time.

* * * * *